United States Patent [19]

Steg, Jr.

[11] Patent Number: 4,490,331
[45] Date of Patent: Dec. 25, 1984

[54] EXTRACORPOREAL BLOOD PROCESSING SYSTEM

[76] Inventor: Robert F. Steg, Jr., 8277 Chapin La., Sunland, Calif. 91040

[21] Appl. No.: 348,338

[22] Filed: Feb. 12, 1982

[51] Int. Cl.$^3$ ............................................. A61M 1/03
[52] U.S. Cl. ....................... 422/46; 128/DIG. 3; 210/321.4; 210/321.5; 422/106; 422/107; 422/113; 422/119; 422/48
[58] Field of Search ...................... 422/44, 46, 48, 106, 422/107, 113, 119; 210/321.3, 321.4, 321.5; 128/DIG. 3

[56] References Cited

U.S. PATENT DOCUMENTS

| | | | |
|---|---|---|---|
| 3,191,600 | 6/1965 | Everett | 128/276 |
| 3,204,631 | 9/1965 | Fields | 128/214 |
| 3,241,295 | 3/1966 | Griffin et al. | 55/165 |
| 3,256,883 | 6/1966 | De Wall | 422/46 |
| 3,489,647 | 1/1970 | Kolobow | 195/1.8 |
| 3,507,395 | 4/1970 | Bentley | 210/443 |
| 3,515,640 | 6/1970 | Rudlin | 195/1.8 |
| 3,526,481 | 9/1970 | Rubricius | 23/258.5 |
| 3,536,451 | 10/1970 | Ludwin | 23/258.5 |
| 3,674,440 | 7/1972 | Kitrilakis | 23/258.5 |
| 3,738,813 | 6/1973 | Esmond | 23/258.5 |
| 3,771,658 | 11/1973 | Brumfield | 210/186 |
| 3,792,978 | 2/1974 | Freedman | 23/258.5 |
| 3,839,204 | 10/1974 | Ingenito | 210/181 |
| 3,849,071 | 11/1974 | Kayser | 23/258.5 |
| 3,877,843 | 4/1975 | Fischel | 417/394 |
| 3,890,969 | 6/1975 | Fischel | 128/214 |
| 3,892,533 | 7/1975 | Freedman | 23/258.5 |
| 3,898,045 | 8/1975 | Bowley | 23/258.5 |
| 3,907,504 | 9/1975 | Hammond et al. | 23/258.5 |
| 3,927,980 | 12/1975 | Leonard | 23/258.5 |
| 3,927,981 | 12/1975 | Vlannay | 23/258.5 |
| 4,015,590 | 4/1977 | Normann | 128/1 D |

(List continued on next page.)

OTHER PUBLICATIONS

*The Journal of Extra-Corporeal Technology*, "Pre-Clinical Evaluation of the Interpulse Membrane Oxygenator", by Massimino et al., vol. 13, #6, 1981, (Official Journal of The American Society of Extra-Corporeal Technology), pp. 283-287.

*The Journal of Extra-Corporeal Technology*, "Counterpulsation-An Alternate Use for the Pulsatile Bypass Pump", by Steven E. Curtis and H. Newland Oldham, Jr., M.D., vol. 13, #6, 1981, (Official Journal of The American Society of Extra-Corporeal Technology), pp. 279-282.

*Primary Examiner*—Michael S. Marcus
*Attorney, Agent, or Firm*—Gausewitz, Carr, Rothenberg & Edwards

[57] ABSTRACT

A unitary system incorporates an upper reservoir container having a blood gas separator, a cardiotomy reservoir and a venous reservoir. The upper container is positioned directly above a lower mass transfer container coupled with the venous reservoir by means of a check valve and having a spirally wound flattened tubular transfer membrane. A vacuum is drawn upon an upper portion of the reservoir container which carries a blood gas separator into which aspirated wound site blood is drawn for filtering and collection of blood in the cardiotomy reservoir. The latter is automatically drained via a pressure responsive valve into a venous blood reservoir at the lower portion of the reservoir container and into which venous blood flows for mixing with the filtered cardiotomy blood. A bladder pump within the mass transfer container above the tubular membrane alternately increases and decreases pressure within the lower container to help draw venous blood from the venous reservoir and to force blood between adjacent windings of the tubular membrane and outwardly from the mass transfer container to an arterialized blood return. The tubular membrane itself is used as a heat exchanger to lower the blood temperature below body temperature and to raise it above body temperature by controlling temperature and increasing thermal conductivity of gaseous oxygen flowing through the tubular membrane and by causing the oxygen to flow at a very high velocity.

18 Claims, 10 Drawing Figures

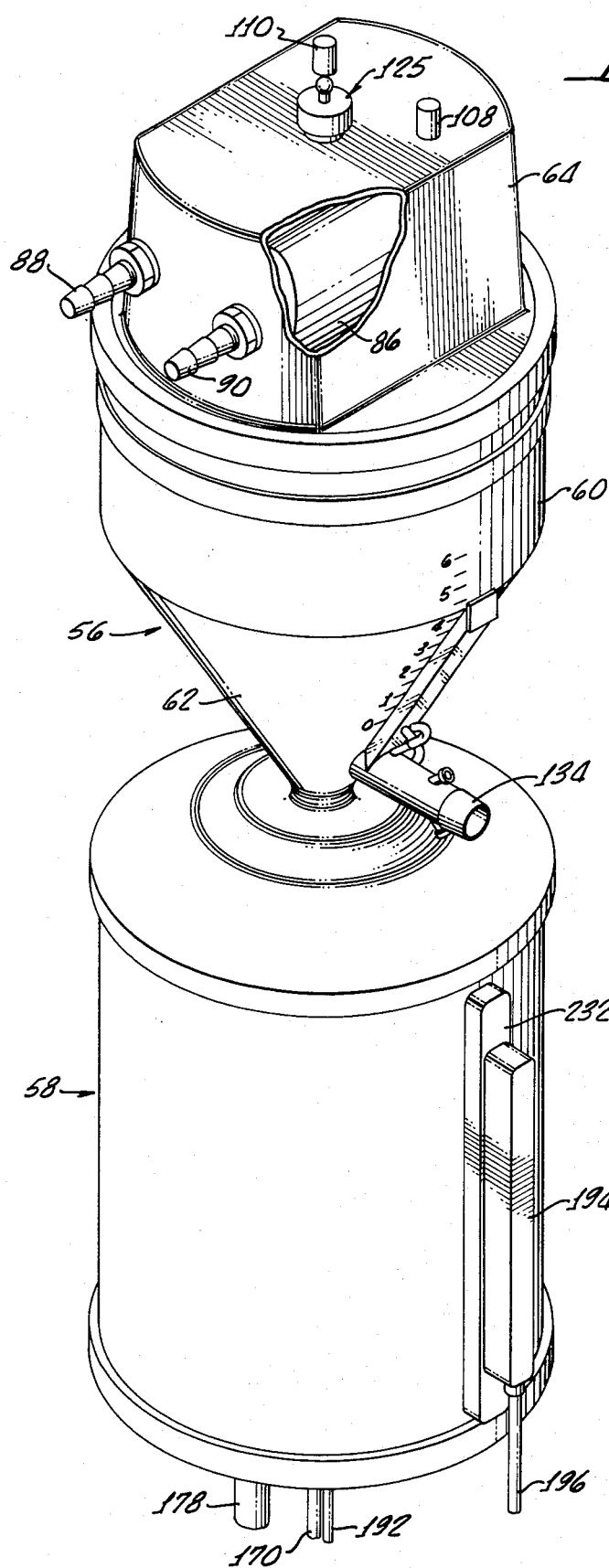
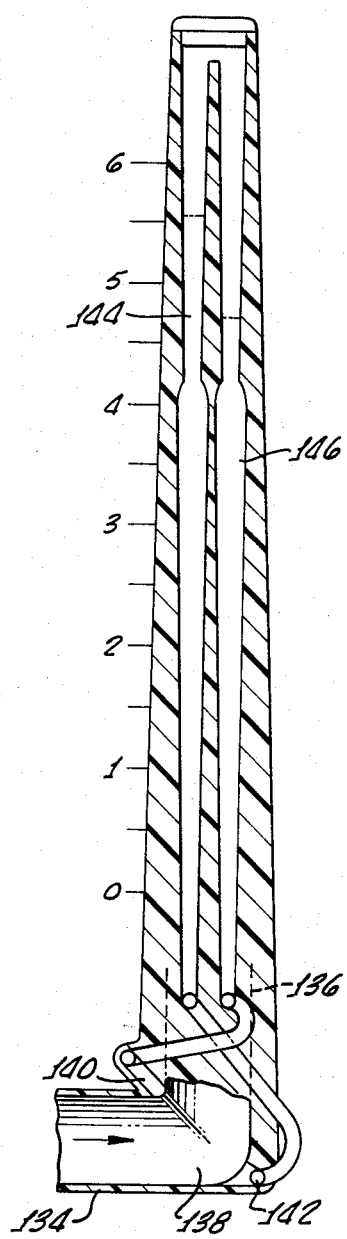
FIG. 2.
FIG. 5.

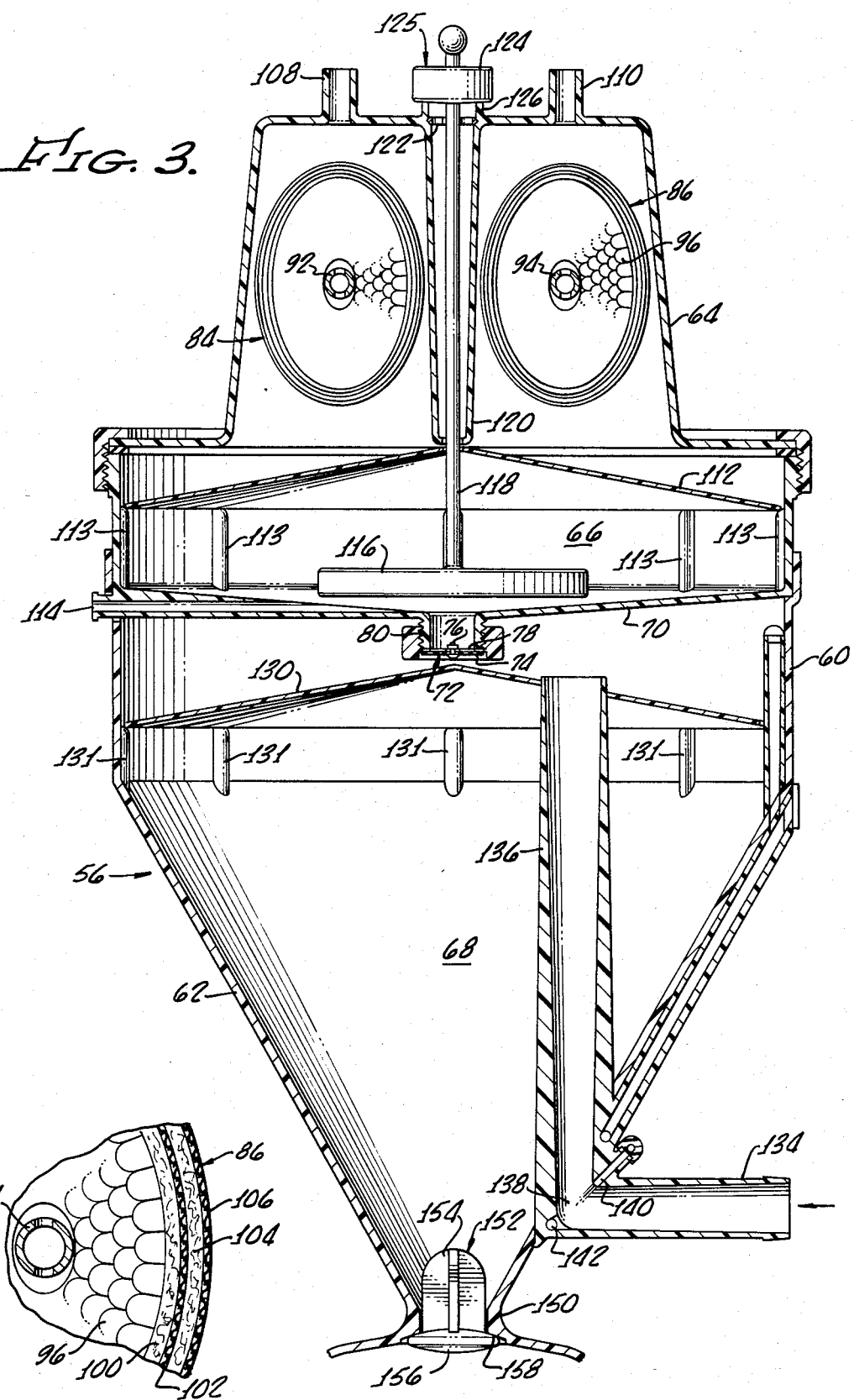

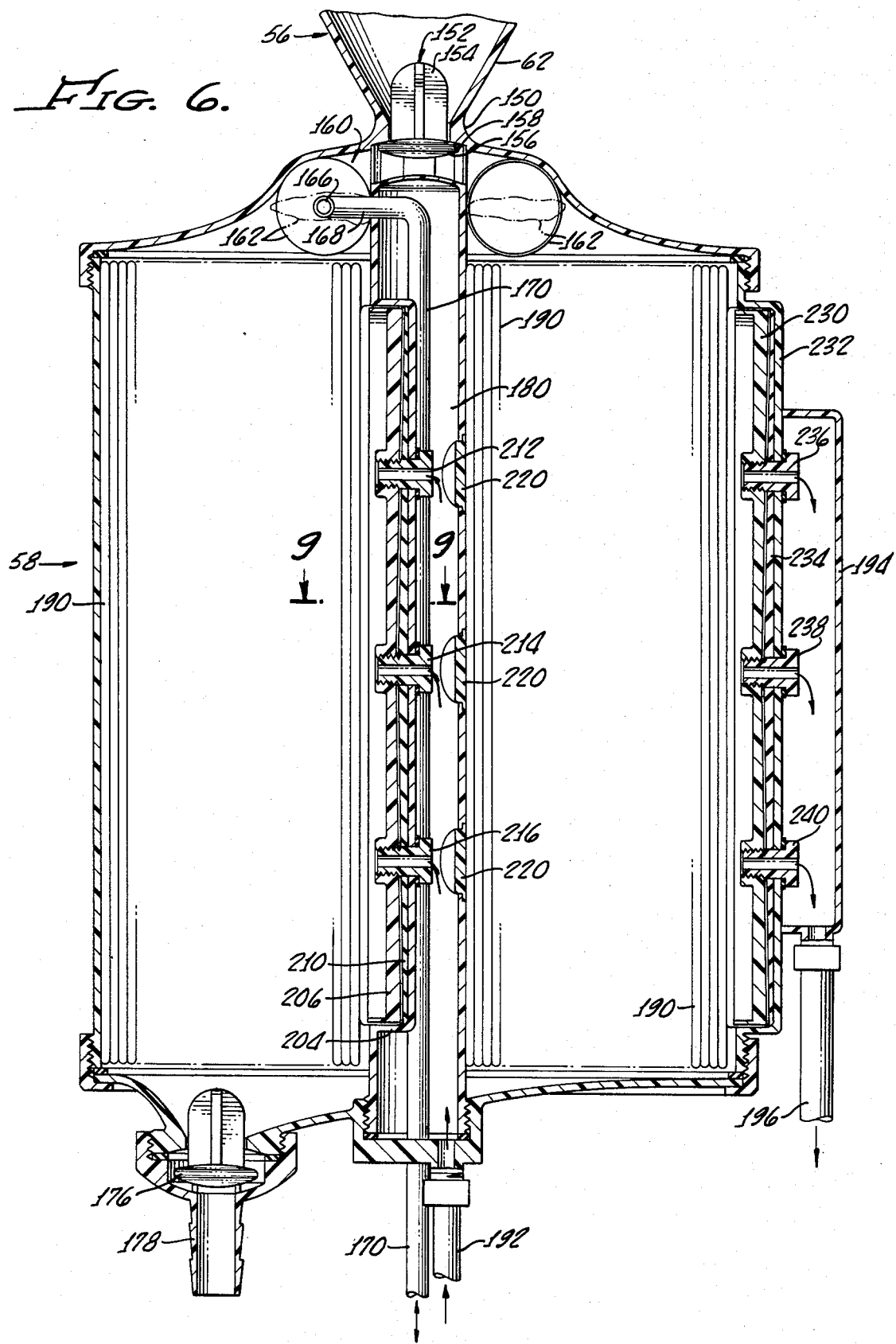

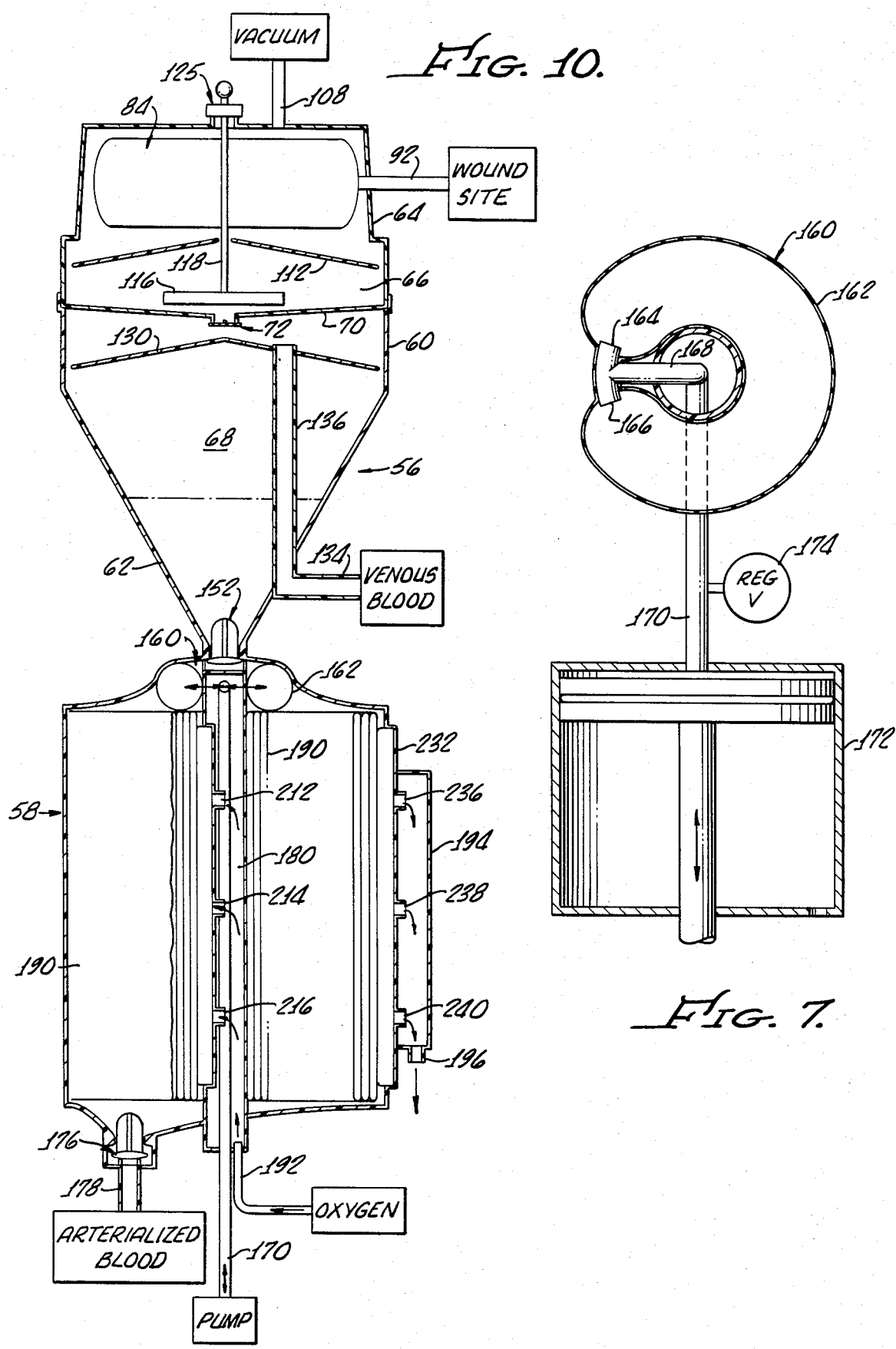

EXTRACORPOREAL BLOOD PROCESSING SYSTEM

BACKGROUND OF THE INVENTION

The present invention relates to blood processing systems and more particularly concerns the overall arrangement and individual components of an extracorporeal system that integrates blood gas separation, cardiotomy reservoir, venous reservoir, oxygenation, temperature control and pumping of the blood.

In membrane oxygenators of the type shown in the patents to Bentley U.S. Pat. Nos. 4,196,075 and 4,094,792 and the patents to Kolobow U.S. Pat. No. 3,489,647, Friedman U.S. Pat. No. 3,792,978, Leonard 3,927,980 and Bellhouse 4,182,653, carbon dioxide from blood on one side of the membrane passes through the membrane into a gaseous oxygen on the other side and oxygen is taken up through the membrane by the blood. Membrane oxygenators of the prior art, although avoiding some problems and limitations of these oxygenators, such as bubblers, employing a direct blood gas interface, introduce a number of problems and disadvantages unique to the membrane-type configuration.

In priming the oxygenator to get it ready for use, a priming fluid must fill the chamber and be recirculated to remove entrapped air. Such oxygenators often require ten minutes or more to insure removal of all entrapped air. In the course of an operation, the extracorporeal blood processing system is often called upon first to lower blood temperature and then to raise blood temperature. Accordingly, most systems employ a heat exchanger for this purpose. Such heat exchangers of prior systems, whether integral with the mass transfer oxygenator, or separate therefrom, are complex and costly, making the manufacture of a disposable system expensive. Prior membrane systems employ high blood pressure differentials that tend to increase blood trauma and lysing of cells.

Excessive arterial blood line pressure or introduction of air into the arterial blood must be avoided at all cost, and improved safety in these areas is always needed.

Although an oxygenator is generally employed with a separate cardiotomy reservoir and venous reservoir, few systems are available that optimally arrange and coordinate these components. Further, cardiotomy reservoir and blood gas separators themselves may introduce excessive blood trauma because of undue forces exerted upon the blood. They may require a separate and independent pump for the reservoir and fail to provide adequate control and regulation of storage and flow. Ventricular pumps employed in some prior systems are difficult to free of entrapped air and peristaltic pumps in prior systems may be a source of additional blood trauma or excess pressure. Thus, there is a need to minimize such problems and provide a fully integrated system having a blood gas separator, a readily regulated cardiotomy storage reservoir, a venous reservoir, and a mass transfer system or oxygenator and heat exchanger of high reliability and relatively low cost.

Accordingly, it is an object of the present invention to eliminate or minimize above-mentioned problems and to provide an extracorporeal blood processing system and components thereof which are efficient, reliable and safe and which minimize blood trauma.

SUMMARY OF THE INVENTION

In carrying out principles of the present invention in accordance with a preferred embodiment thereof, a blood oxygenator has a mass transfer membrane dividing a container into first and second chambers and valving is provided for passing blood into and out of the first chamber and for passing gaseous oxygen into and out of the second chamber. A bladder pump having a sealed, inflatable and collapsible membrane is mounted within the first chamber for inflation and deflation within the chamber. According to another feature of the invention the mass transfer membrane comprises a tube wound about a longitudinal axis of the container and which is collapsed by decreased pressure to facilitate priming of the oxygenator and removal of air. The mass transfer system is used as a heat exchanger to raise or lower blood temperature above or below body temperature by appropriately changing temperature of the gaseous oxygen flowing through the tubular membrane and by flowing the oxygen at a very high velocity. Thermal conductivity of the gaseous oxygen is increased by dispersing therein a material having a higher thermal conductivity.

According to another feature of the invention, a self-regulating blood gas separator and cardiotomy reservoir comprises a container having a cardiotomy reservoir chamber therein, a blood gas separator in a portion of the reservoir chamber, means for coupling a vacuum source to the chamber, means for introducing blood into the separator and a pressure operated valve in a lower portion of the chamber to flow blood from the chamber upon increase of pressure within the chamber. A unique feature of the blood gas separator and cardiotomy reservoir is a float operated valve responsive to the level of blood in the reservoir for changing the pressure to control operation of the pressure operated valve.

BRIEF DESCRIPTION OF THE DRAWINGS

FIG. 2 is a pictorial illustration, with parts broken away, of the blood processing container with its blood separator, cardiotomy and venous reservoirs and mass transfer system;

FIG. 3 is an elevation sectional view of the upper section of the container of FIG. 2;

FIG. 4 is an enlarged fragmentary view of a portion of the blood gas separator;

FIG. 5 is a schematic illustration of the venous blood flow rate indicator;

FIG. 6 is an elevation sectional view of the mass transfer section of the container of FIG. 2;

FIG. 7 schematically illustrates the bladder pump and its drive;

FIG. 10 is a sectional view of the extracorporeal blood processing system described herein.

DETAILED DESCRIPTION OF THE PREFERRED EMBODIMENTS

Figure 1:
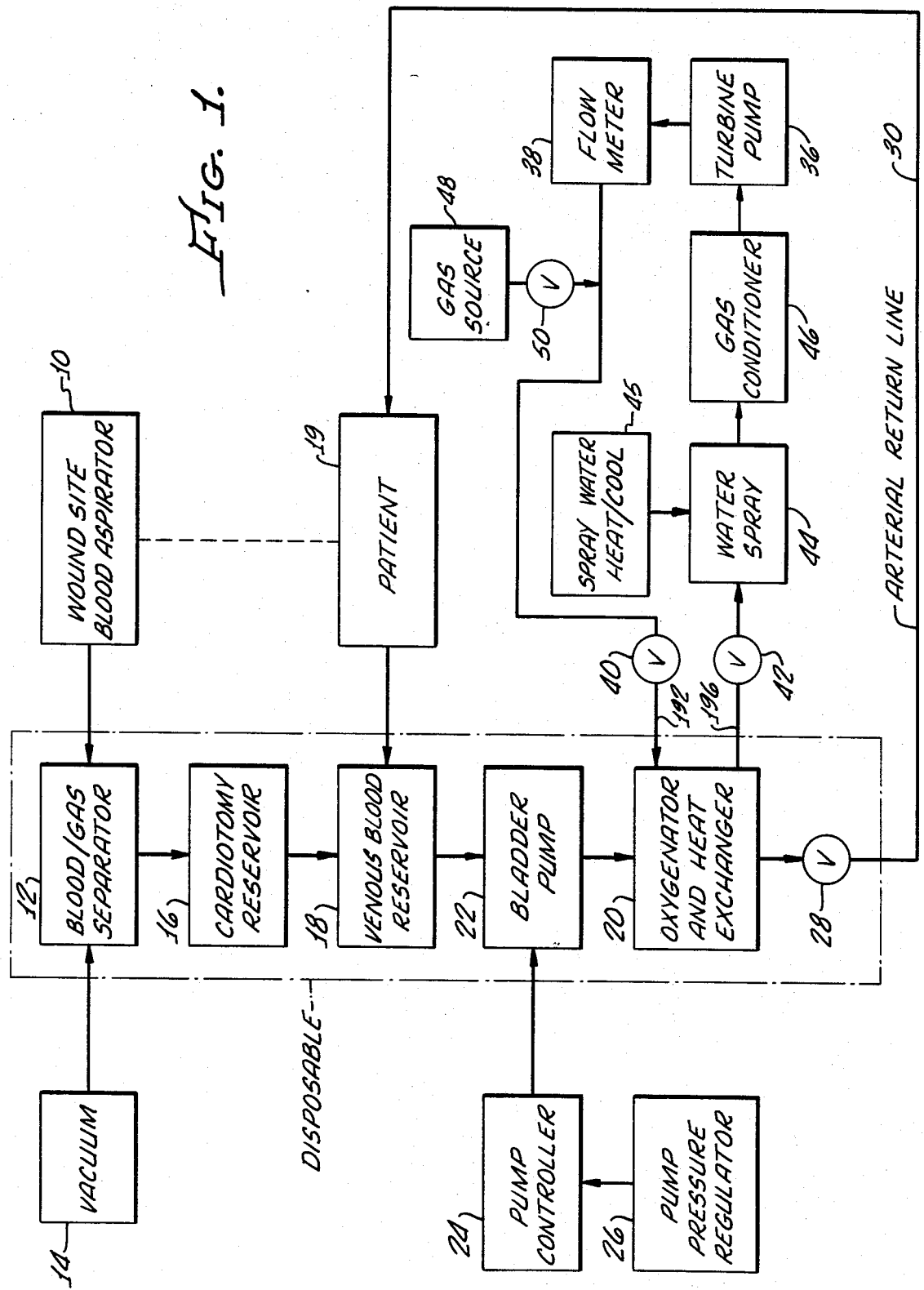
FIG. 1 is a functional block diagram illustrating components of an extracorporeal blood processing system embodying principles of the present invention.

Functionally illustrated in FIG. 1 are major components of an extracorporeal blood processing system embodying principles of the present invention and primarily intended for use during surgery. Blood from a wound site aspirator 10 is drawn into a blood gas separator 12 by means of a vacuum source 14 which lowers the pressure within the separator. Air, foam and other impurities are filtered from the blood in the separator and the liquid blood is collected in a cardiotomy reservoir 16 from which it is fed to a venous blood reservoir 18 which also receives venous blood from a patient, indicated at 19.

Blood from the venous reservoir 18 is fed into a combined oxygenator and heat exchanger 20 under control of a bladder pump 22 which is operated by a pump controller 24 and pump pressure regulator 26. Oxygenated and temperature controlled blood from the oxygenator and heat exchanger 20 is fed through an output valve 28 and thence through an arterial return line 30 back to the patient.

The oxygenator and heat exchanger 20 includes a gaseous oxygen flow path connected in a closed circuit in which gas is recirculated by means of a turbine pump 36. The pump drives conditioned gaseous oxygen (or an air/oxygen mixture) through a flow meter 38 and thence through a valve 40 at the input to the gaseous oxygen flow path of the oxygenator and heat exchanger. Gas exiting from the oxygenator and heat exchanger flows through a valve 42, thence to a water spray device 44, where a heating or cooling spray of distilled water is injected to saturate the gas, increase its thermal conductivity, and raise or lower its temperature. Temperature of the water is controlled by a heating and cooling device 45, which may take the form of a heat pump and evaporator. The saturated gas is then fed to a conditioner 46 in which carbon dioxide is removed and the gas disinfected. The conditioned gas from conditioner 46 is fed as the input to turbine pump 36. The appropriate amount of gas within the closed gas recirculating system is established with the aid of a source of gaseous oxygen 48 connected by a valve 50 to the gas flowing from meter 38.

The oxygenator is formed of a spirally wound, flattened, tubular membrane more particularly described below, through which the gaseous oxygen flows at high velocity. Blood flows between layers of the wound tubular membrane to enable exchange of oxygen and carbon dioxide through the membrane. Temperature controlling device 44 lowers or raises the gaseous oxygen temperature so as to lower the temperature of arterialized blood in return line 30 below body temperature or to raise the temperature of such blood above body temperature, as desired. The ability of the mass transfer membrane itself to act in the dual role of oxygenator and heat exchanger is enabled by causing the gaseous oxygen to flow through the mass transfer system at an exceedingly high rate. In addition, thermal conductivit7y of the gas is increased by the same mechanism that controls its temperature. Although prior membrane oxygenators employ gas flow rates of less than one-half meter per second, it is necessary that much much greater velocities be employed in order to enable the gas to produce any significant amount of temperature change of the blood. It is found that the flow rate of the gaseous oxygen through the gas chamber of the mass transfer system must be about 5 and 30 meters per second. Preferably, a flow velocity of 13 meters per second is employed. Flow rates below about 5 meters per second will accomplish little significant temperature change of the blood in a mass transfer membrane system having a gas flow path of a reasonable length such as, for example, about seven meters. Flow rates significantly higher than about 30 meters per second may require too much energy, and produce too great a pressure drop across the gas compartment. The minimum flow rate of 5 meters per second is many times higher than the maximum gas velocity of no more than 0.5 meters per second in prior art systems where the gas is employed solely for oxygenation.

At a gaseous oxygen flow rate of about 13 meters per second the oxygen temperature may be lowered to about 25° C. by the cooling device 44 and, in the oxygenator described herein, will produce arterialized blood of about 25° C. Similarly, gaseous oxygen heated to 42° C. or more by the heater 44 will produce arterialized blood from the described heat exchanger and oxygenator at a temperature of not more than 42° C. Thus, no separate or costly heat exchanger need be employed, nor need any additional heat exchanging apparatus be built into the oxygenator itself.

The ability to use the same gas both for mass transfer and as the heat exchange medium itself derives in large part from the greatly increased flow velocity of the gas. Important physical conditions affecting such heat transfer in the described system include thermal conductivity of the gas, its viscosity, density, specific heat and the boundary layer conditions, such as the thin film coefficient of the gas. Thermal conductivity of the gas is increased by dispersing within the gas particles of a material having a much higher thermal conductivity than that of the gas. In the arrangement illustrated in FIG. 1, this higher thermal conductivity material is water, or water vapor. Preferably, the gas is saturated with the water vapor to maximize increase in thermal conductivity. Supersaturation with water or water vapor may be achieved by cooling the saturated gas/water vapor mixture immediately after heating it with the water vapor. The injected particles themselves perform two important functions, as they both increase thermal conductivity of the gas and change its temperature.

To increase thermal conductivity of the gaseous oxygen, particles of materials other than, or in addition to, water may be mixed with or suspended in the gaseous oxygen. For example, injection of microscopic beads of polyolefin, or equivalent material, having a size in the range of 10 to 150 microns will increase thermal conductivity of the resulting gas-solid dispersion by several times, when compared to water saturated gas alone. Solid materials with higher thermal conductivity than polyolefins may also be employed. Preferably, such materials are low or non-hygroscopic. Materials of low abrasion characteristics are preferred to reduce wear on the gas turbine and other permanent components of the system.

Elements 12, 16, 18, 20, 22 and 28 shown within a dotted box in FIG. 1, form disposable elements of a blood processing system embodying principles of the present invention. As shown in FIG. 2, all of these elements are incorporated in a dual section unitary container having an upper section 56 integrally connected with a lower section 58, and all made of a hard, rigid and preferably transparent plastic, such as a polycarbonate or the like.

Upper section 56 (FIG. 3) is formed of a rigid housing having a generally cylindrical upper portion 60, and a generally conical lower portion 62 with a generally rectangular blood gas separator section 64 threadedly connected and sealed to upper portion 60. Upper container section 56 is divided into an upper, or cardiotomy, chamber 66 and a lower chamber (including a venous reservoir 68) by means of a horizontally extending portion 70 having a depressed central section in which is mounted a pressure operated valve 72. Valve 72 comprises a relatively large flexible rubber diaphragm 74 secured at its center 76 to a spider 78 fixed in a downwardly extending port 80 at a central area of partition 70.

Mounted in blood gas separator section 64 are a pair of side-by-side, elongated and generally horizontally extending two-phase blood gas separators 84, 86 which are connected by fittings 88, 90 (FIG. 2) to perforated distributor tubes 92, 94 that extend along the center of the separators and filters. The fittings are connected by tubing (not shown) to aspirator tips at the wound site. Each separator filter 84, 86 comprises a large horizontally extending substrate formed by the surface of a polyurethane mesh 96 upon which is dispersed a silicone surfactant that helps to destabilize the mixture of blood and foam from the aspirated wound site. Surrounding each polyurethane substrate is a course mesh 100 (FIG. 4) which helps to reduce pressure gradients between the substrate and a primary blood filter 102 which surrounds the mesh. A second course mesh 104, surrounds the primary filter 102 and in turn is surrounded by a second filter 106 which forms the outer surface of the separator.

Vacuum source 14 (FIG. 1) is coupled to the interior of the blood gas separator section 64 by means of vacuum fittings 108, 110 to maintain a relatively low vacuum pressure within the blood gas separator chamber. Thus, the vacuum source, which is located downstream of the two-phase separators 84, 86 draws the blood foam mixture through the separators and, as blood bubbles burst, the liquid portion tends to collect in the bottom of the substrate while the gas portion rises toward the top of the substrate to be extracted through the vacuum fittings. The arrangement provides flow of blood in a generally horizontal direction, at right angles to the primary blood filter 102. The filtered blood flows through the second course mesh surrounding the primary filter 102 which further reduces the pressure gradient and thence through the second filter 106 which has an effective pore size smaller than that of primary filter 102.

Blood which is has been degassed and filtered then collects by gravity, flowing downwardly to impinge upon a centrally apertured conical baffle 112 which extends across the upper chamber 66, above partition 70, and inclines outwardly and slightly downwardly toward but just short of the outside walls of the container. A number of ribs 113 fixed to the interior of the container portion 60 support the outer circumferential edge of baffle 112. Blood flow velocity is decreased by the relatively gentle slope of the baffle. The filtered, degassed blood then collects in the cardiotomy reservoir defined by chamber 66 above the partition 70. A fitting 114 is provided in a lowermost portion of chamber 66 to enable blood to be drawn from the cardiotomy reservoir for further processing if desired.

A float 116 is connected to the end of a float rod 118 which extends upwardly through the container section 64 and through the aperture in baffle 112, guided by a tubular guide 120 and an upper guide 122, and adjustably connected at its upper end to a valve closure member 124 of a pressurizing valve 125. Valve 125 is normally closed with member 124 resting upon a valve seat 126 on the top of container portion 64 so that if the closure member 124 is raised from the seat the interior of the chamber 66 is in communication with ambient atmosphere to thereby decrease the amount of vacuum within the chamber. Valve member 124 is slidably adjustable along the length of float rod 118 so as to adjust the level at which the float will operate the pressurizing relief valve 125.

The cardiotomy reservoir is normally under a small decreased pressure because of the vacuum drawn via fittings 108 and 110, and such decreased pressure operates to maintain the flexible pressure operated valve 72 closed, because the area below partition 70 is at atmospheric pressure. As blood from the wound site collects within the cardiotomy reservoir and the level of blood therein rises, a point will be reached at which float 116 also rises to thereby raise valve closure 124 and cause ambient air to be admitted to the interior of the chamber. As the vacuum within cardiotomy chamber 66 decreases, valve 72 no longer remains closed and blood will then drain from the cardiotomy reservoir chamber 66 downwardly and outwardly through the fitting 80.

Adjusting the closure member 124 along the float shaft 118 allows adjustment of the float so that, for example, if it is desired to continuously drain the processed cardiotomy blood from the chamber 66, the float level is set at its lowest point, that is, valve closure 124 is moved to an uppermost point along the float rod 118 so that the float 116 is at a lowest point when the valve 125 is closed.

The negative pressure needed for blood wound site aspiration is relatively low, although the conductance, or rate of flow, must be relatively high to keep the wound site dry. When the aspirator suction tip is removed from the wound site (as occurs frequently during an operation), air enters the suction tip. The described arrangement allows one of two things to occur in such a situation. If constant draining of the cardiotomy reservoir is desired, the pressure within chamber 66 is allowed to increase (toward ambient atmospheric pressure) thus insuring that valve 72 is open and that the cardiotomy reservoir will drain. However, if the reservoir level is desired to be controlled by the float, then the pressure must remain the same even though air is sucked into the suction tip of the aspirator. Accordingly, for such a situation, controls of the air-driven vacuum pump 14 are established to sense the decrease in vacuum and to increase the pump speed so as to supply additional conductance. Therefore, chamber 66 remains below atmospheric pressure and valve 72 remains closed until the float rises to open valve 125. The valve seat 126 is sufficiently large to cause the pressure within chamber 66 to rise to atmospheric pressure even though the vacuum pump provides a limited amount of increased conductance. Both the amount of vacuum pressure and the volume of conductance can be readily varied by control of the vacuuum pump in conventional fashion.

The float 116 may be adjusted to insure that a significant volume of blood, up to an amount in the order of about 3,000 milliliters, for example, may be stored before it is automatically drained from the pressure responsive valve 72. Alternatively, blood may be retained within the cardiotomy reservoir for removal via fitting 114 by an additional pump (not shown) into a blood processing system, such as blood washing cyclone, for later return of heavier washed blood components to the systemic circulation. This additional processing of the blood may avoid introduction of large amounts of traumatized blood into the circulation. Blood returned from the wound site is believed to be a major source of hemolysis. Thus, the additional processing may help to remove lysed cells and other lightweight components and reduce the impact of a major cause of hemolysis in cardiac surgery.

Cardiotomy blood exiting the cardiotomy reservoir pressure operated valve 72 falls upon a second radially outwardly and slightly downwardly inclined conical baffle 130 extending across an upper portion of the lower container of the cylindrical container section 60. A number of circumferentially spaced ribs 131 fixed to the inner surface of container portion 60 support the outer peripheral edge of baffle 130. The edges of baffle 130 are spaced from the inner surface of the container walls whereby the blood will flow at decreased velocity toward the container walls and then downwardly along the conical walls of the lowermost container portion 62 which defines the venous reservoir 68 that operates substantially at atmospheric pressure. Venous blood from the patient is fed into the venous reservoir via an angulated input tube having a horizontally and outwardly extending tube section 134, which is adapted to be connected to a line to the patient, and a vertical tube section 136 extending upwardly through the venous reservoir, penetrating the baffle 130 at a point slightly displaced from its center and terminating just above the baffle. Venous flood flows through the elbow, or right angle bend 138 at the intersection of inlet tube sections 134 and 136, and then flows out to the upper surface of baffle 130 where it is mixed with cardiotomy blood to flow outwardly and downwardly to the walls of the venous reservoir and thence for collection at the bottom of the venous reservoir. Blood is discharged from the upper end of inflow tube 136 upon the conical baffle so as to reduce blood velocity, thereby reducing trauma and permitting removal by gravity of entrapped air that occasionally enters from the venous line.

A venous flow meter is provided by connecting at inner and outer sides 140, 142, respectively, (FIG. 5) of the elbow 138, first and second legs 144, 146 of a dual manometer having the legs interconnected at their upper portions. Because of the centrifugal force of the inflowing blood, which makes a 90° turn at elbow 138, there is a differential pressure at inner and outer elbow sides 140, 142 which shows up as different levels of blood in the manometer legs 144, 146. The difference in blood levels in the manometer tubes is quantitatively measured with the aid of a scale (FIG. 2) marked on the outside of the conical venous reservoir. The higher the velocity of the inflowing venous blood, the higher the centrifugal pressure on the outer side of elbow 138 and the greater the difference between the blood levels in tube 144, 146.

The lowermost end of the venous reservoir container portion 62 (FIGS. 3 and 6) has a narrow neck 150 which merges with the generally conical upper surface of the lower container section 58 (FIG. 6). Positioned in the narrow neck portion 150 is a relatively large area, low mass check valve 152 having a cross-shaped stem 154 and a valve closure 156 adapted to move upwardly to seat upon a downwardly facing valve seat 158 formed in the venous reservoir neck 150.

Mounted within the uppermost conical portion of the lower container section 58 (FIG. 6), immediately below check valve 152, is a bladder pump 160 formed of a sealed flexible tubular membrane of nearly toroidal shape, extending approximately 270 degrees, as best seen in FIG. 7. A T-shaped gas supply tube has arms 164, 166 extending into opposite end portions of the membrane 162 and has a central stem 168 connected with a supply conduit 170 that connects to a variable stroke pump 172. Pressure within the bladder pump membrane 162 is controlled by a suitable regulator 174. Accordingly, both pressure within the bladder pump 160 and the volume of its stroke may be independently controlled.

Lower container section 58 (FIG. 6) forms a closed sealed chamber having input check valve 152 at its uppermost portion and, at its lower portion, having a similar output check valve 176 which communicates with a fitting 178 to which is connected the arterial return line 30 (FIG. 1).

Fixedly mounted within and extending axially from top to bottom of the mass transfer container section 58 is a central mandrel 180 to which is fixedly connected (by means more particularly described below in connection with FIGS. 8 and 9), the inner end of a flattened, spirally wound tubular membrane 190. The tubular membrane has a length of about 7 meters and a width, when flattened and wound about the axial mandrel 180, of about 25 centimeters, extending vertically from the bottom of the lower container section to a point just below the bladder pump 160. Bladder pump input tube 170 extends through the mandrel for connection to the pump input conduit section 168. The mandrel forms a manifold having gaseous oxygen input tube 192 connected to one end. The manifold is coupled to the innermost end of the tubular membrane by several manifold fittings shown in detail in FIGS. 8 and 9. Corresponding fittings are mounted to the outermost end of the tubular membrane and adapted to be connected by means of a manifold 194 (FIG. 6) with a gaseous oxygen flow line 196 to flow the exiting gaseous oxygen through valve 42 to the gas heater and cooler 44 (FIG. 1). A course mesh 200 (FIG. 8) is positioned within the tubular membrane to insure turbulent flow of gas abbd to prevent complete collapse of the membrane and blockage of the spiral gaseous path within the tube.

The mass transfer member is a conventional-type material such as a silicone or a polyolefin membrane.

Figure 8:
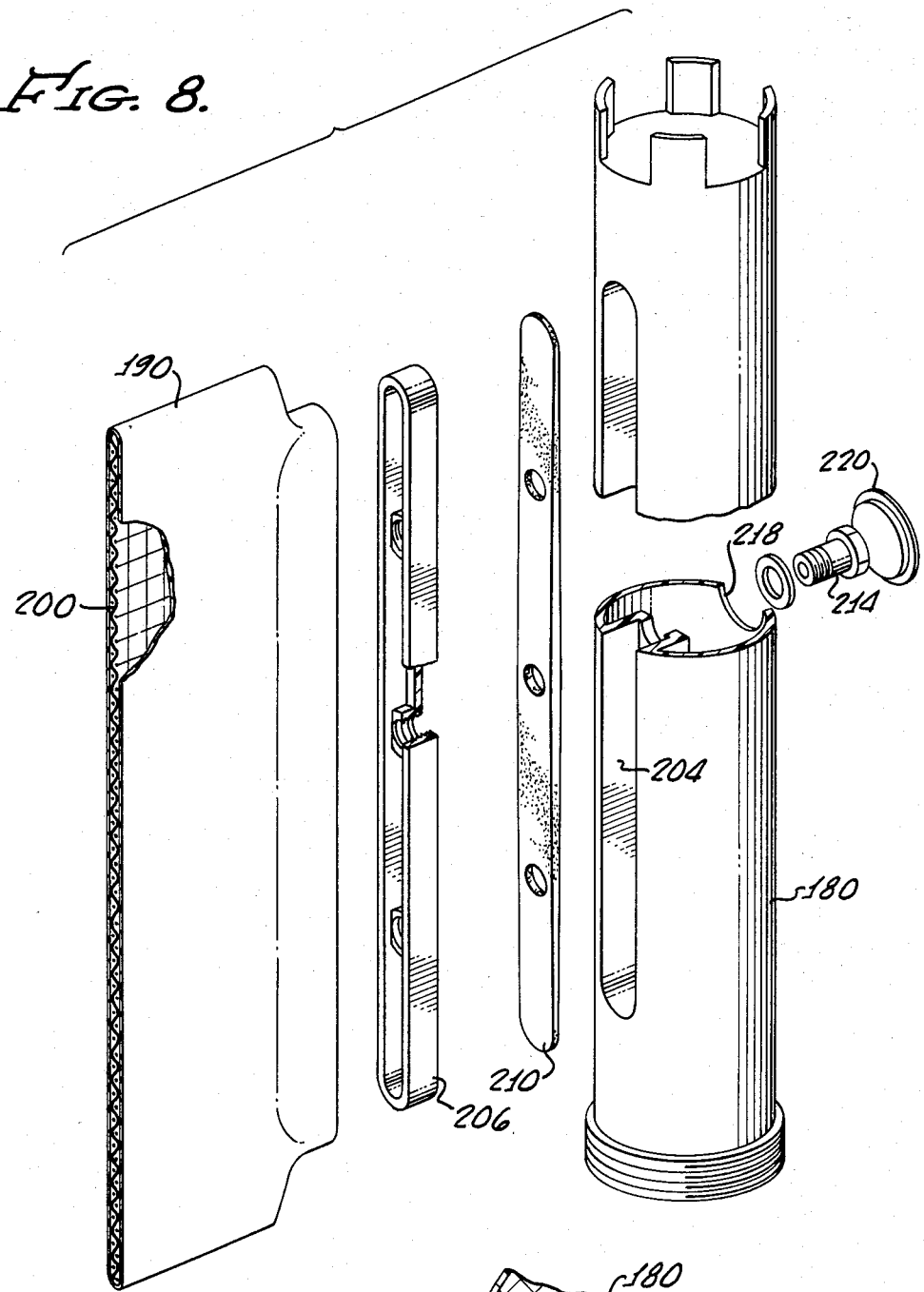
FIGS. 8 and 9 show details of the end connections for the spirally wound tubular membrane.
Figure 9:
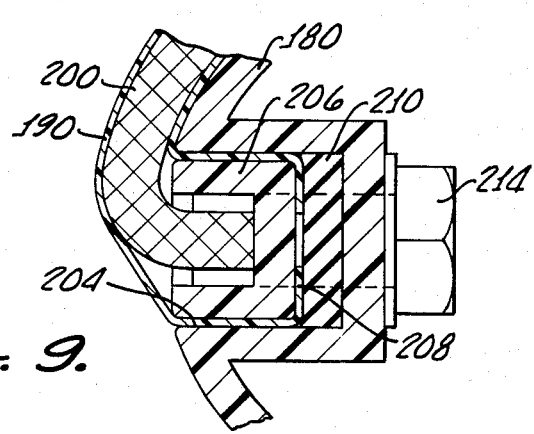

As can be seen in FIGS. 8 and 9, the central mandrel and manifold 180 is formed with an inwardly recessed slot 204 which receives a flattened collar 206 over which the end of the membrane 190 extends. The end edge 208 of membrane 190 extend over the ends of the flattened collar 206 and is sealed between the collar and the mandrel 180 by means of an interposed elongated gasket 210. Mesh 200 extends into the flattened collar 206 (FIG. 9). Headed tubular fittings 212, 214, 216 are threaded into the collar 206 and extend through slot 204 into the mandrel 180 so that the assembly may be held together by the hollow headed externally threaded fittings which communicate with manifold 180 which in turn is in communication with the gaseous oxygen input conduit 192. The several fittings are inserted through mandrel holes 218 which are thereafter sealed by flexible discs 220. The arrangement provides for a mechanical sealing connection of the end of the tubular membrane and avoids the need for adhesive sealing compounds on the membrane and their inherently required curing time during manufacture. A substantially similar mechanically sealed end connection of the outermost end of the tubular membrane is provided at the exterior of container section 58.

The outermost end of the membrane tube extends over and around a flat elongated receiver 230 (FIG. 6) and has its end edges folded over the outer surface of the receiver and temporarily held in such position while the receiver is pressed up against the outer wall 232 of the container section 58 and sealed by means of a flat elongated gasket 234 interposed between the receiver and the wall 232. Headed hollow fittings 236, 238, 240 are threaded into the receiver 230 and all communicate with the interior of the tube end. The fittings extend through apertures in the wall 232 into the manifold 194 so that the gas can flow through the fittings into the manifold which is connected with the gaseous oxgyen flow line 196 for exiting gas.

The tubular membrane 190 divides the interior of the lower section 58 of the container into two chambers, the first or gas chamber being the interior of the tube which forms a spiral gaseous oxygen chamber, and the second or blood chamber, being the volume within the container section outside of the tube. The blood chamber includes a number of vertical blood flow paths formed between adjacent spiral windings of the tube. Thus, the blood flows from the input check valve 152 (FIG. 6) to the uppermost ends of the tubular windings, thence vertically downwardly between adjacent windings to flow outwardly through the lowermost check valve 176.

Both check valves 152 and 176 have a specific gravity close to that of blood and a low mass to thereby reduce shear effects at the valve seats. The valves themselves are of a relatively large area, thereby also minimizing blood shear and pressure gradients. During original priming of the mass transfer system the valves 152 and 176 are both open. These valves are operated either by differential pressures across the valve, or, in the absence of such differential pressure, by gravity. Gravity will act on the valves to hold them open when the system has no liquid. Appropriate priming solution may be fed into the pumping chamber above the mass transfer membrane from the venous reservoir, or from the cardiotomy blood processor by gravity. During priming, a vacuum is drawn on the interior of the tubular mass transfer membrane so as to substantially collapse this membrane upon the coarse mesh contained within it. This collapsing of the membrane helps to expand the blood flow paths between adjacent membrane windings to facilitate removal of entrapped air. There is no need for extensive recirculation of the priming solution to move the entrapped air as in other membrane systems. The negative pressure on the gas side of the membrane during priming not only opens the blood passages but reduces resistance to the flow of priming solutions. During the priming the bladder pump is held in a deflated, or collapsed, position by the system controls.

In operation, the bladder pump is driven by compressed gas in a closed circuit including the pump 172, conduit 170 and the bladder 162 itself. This prevents more than a few millimeters of gas from the closed circuit from entering the blood circuit should a rupture develop in the pump bladder. As previously mentioned, the displaced volume of blood may be varied by varying the stroke of the pump 172 (FIG. 7) and the driving pressure may be independently varied by adjustment of the regulator 174. These features have the advantage of limiting the maximum pressure in the arterial return line. If an accidental occlusion of the arterial line should occur, there will be no bursting of the arterial line or disconnection of the tubing connectors, nor will the transfer membrane be damaged.

The bladder pump itself introduces less blood trauma, because no mechanical rubbing of the bladder with a seat or conduit occurs as in occlusive peristaltic pumps. It operates by increasing and decreasing pressurization of the relatively incompressible blood with which the blood chamber within container section 58 is filled during operation of the system. As gas from pump 172 is introduced into the bladder pump it expands, increasing the pressure on the incompressible blood within the blood chamber to thereby force the venous inlet valve 152 closed and to force the arterial output valve 176 open. In addition, the increased pressure within the blood chamber forces the blood through the blood paths between tubular membrane windings and into the arterial return line 30. Upon deflation of the bladder pump, to the position illustrated in dotted lines in FIG. 6, pressure within the blood chamber of container section 58 decreases, thereby closing outlet valve 176 and opening venous inlet valve 152 to draw venous blood into the chamber.

The venous reservoir container is rigid to permit an accurate assessment of blood contained therein at any time and to permit air to flow through the venous valve between the venous reservoir and the bladder pump chamber should the level of blood within the venous reservoir drop below minimum safety levels.

The use of the bladder pump provides an inherently fail-safe system with respect to inadvertent pumping of air with the pumped blood and prevents a potentially catastrophic embolism. Because the pump is operable only upon a relatively incompressible fluid, it becomes disabled upon entrance of air into the blood chamber of container section 58. Should the chamber contain air, the inflation stroke of the bladder pump does not significantly increase the pressure within the blood chamber. Therefore, blood is not pumped and air in the upper portion of the chamber is not mixed with blood and pumped between the windings of the tubular membrane. Further, with air in the pumping chamber the input valve 152 remains open so that the pump merely moves air into and out of the rigid, noncollapsible venous reservoir, assuming that the lack of blood in the venous reservoir was the cause of the entrance of air into the pumping chamber.

Cycling of the bladder pump may be triggered from a suitable electrical signal which may be derived from the patient's electrocardiogram, or from an internal clock of the system control.

The bladder pump may be used for counter pulsation as described in the prior art. However, a surprising and unusual advantage derives from the use of the bladder pump within the blood chamber and very close to the blood flow paths along the membrane. This advantage is the increase in mass transfer obtained by reduction of the thickness of blood layer at the blood-membrane boundary. The Reynolds number of the blood flowing at its average velocity through the blood chamber is below that for turbulent flow. Laminar blood flow at such relatively lower velocity results in a relatively thicker blood to membrane boundary layer and, therefore, a relatively lower mass transfer across the membrane. The bladder pump, particularly at higher frequencies, produces pressure pulses of very short rise and fall times and having greater peak to peak amplitudes. This effect is enhanced at the blood flow paths between membrane windings because the pump is so close to the mass transfer membrane that there is very little pressure drop between the pump and the blood paths. The pressure pulses are dampened toward the downstream end of the mass transfer blood flow paths and in the arterial blood tubing and filters downstream of the mass transfer container. The very small pressure drop between the bladder pump and the proximate blood flow paths allows the sharp, higher frequency pressure pulses of the bladder pump to impose a secondary, pulsating and higher peak velocity component upon the average blood velocity to thereby decrease the blood to membrane boundary layer and increase mass transfer. Pump rate may be raised to between one and two hundred cycles per minute to increase mass transfer.

Although the disclosed spiral membrane configuration is preferred, advantages of the described bladder pump and blood chamber combination may also be employed in mass transfer systems with non-spiral membranes, such as parallel plate or hollow fiber mass transfer devices.

As venous blood enters the blood chamber of container section 58, just above the bladder pump, and flows axially downwardly through the annular passageways between the membrane windings, mass transfer occurs along the blood path because the blood entering the venous inlet of the mass transfer chamber has a relatively low oxygen content and a relatively high carbon dioxide content. The gas side of the membrane within the flattened tube has a relatively high oxygen and relatively low carbon dioxide content and may have a temperature that is higher or lower than that of the blood side. The semipermeable membrane is permeable to oxygen, carbon dioxide, and nitrogen, but is not permeable to blood or liquid water and, accordingly, the appropriate exchange of gases takes place across the membrane as the blood flows on one side and the gaseous oxygen flows on the other.

Further, during cardiac surgery the blood temperature may be of a lower or higher temperature than desired. As previously mentioned (in connection with the description of FIG. 1), if the gaseous oxygen temperature is set at about 42° C., the relatively cool venous blood will be warmed to 42° C. by the time it leaves the blood chamber. Similarly, if the incoming venous blood is at body temperature, 37° C., it can be readily cooled to about 25° C. by setting the temperature of the incoming gaseous oxygen at 25° C. In order to achieve this temperature change, and because of the relatively low thermal conductivity and specific heat of the gaseous oxygen, the flow velocity of the gaseous oxygen is set at about 13 meters per second, as described above.

There are upper temperature limits (42° C.) that can be applied to blood and there is also a maximum temperature differential of 10° C. between blood and its contact surface at any given time for heating. Because of the lower thermal conductivity of the blood heating medium (gaseous oxygen) in the described arrangement, when compared to liquids used in prior heat exchange systems, the present arrangement may employ a ventilating/heating gas temperature well above the 42° C. limit. The gaseous oxygen heat exchange medium may have a temperature as high as 50° to 55° C. before the contact surface of the spiral membrane is itself heated to 42° C. Accordingly, the resultant temperature gradient and high gas velocity, particularly when the gas is combined with dispersed particles of liquid or solid, will significantly enhance efficiency of the described heat exchanger. In such an arrangement a disposable temperature sensing thermistor may be employed upon the surface of the spiral heat exchanger membrane at the gas inlet to monitor temperature of the membrane surface.

An important cause of blood trauma is shear induced cell lysing which may be produced by the processing system itself. A conventional blood gas separator of the type used in bubble oxygenators may have localized high shear, especially with down-flowing blood gas separator systems. The apparatus shown in the present disclosure employs a number of techniques to minimize shear forces including, for example, the horizontally oriented two-phase blood gas separator, the low pressure vacuum cardiotomy suction, the elimination of shear inducing peristaltic pump by the use of a nonoccluding expanding bladder pump having large area, very low pressure gradient check valves on both arterial and venous sides of the device, and the very low pressure gradients across the blood side of the mass transfer membrane.

There has been disclosed an extracorporeal blood processing system having disposable components that provide efficient heat, oxygen and carbon dioxide transfer, and a membrane mass transfer device utilizing the membrane alone without additional heat exchangers. The apparatus also provides, in a unitary configuration, an improved blood gas separator and self-regulating cardiotomy reservoir together with a venous reservoir that uniquely cooperates both with the cardiotomy reservoir and the pumping action of the mass transfer system, all arranged so as to make the disposable components relatively economical to manufacture, efficient to operate without introducing significant blood trauma, eash and fast to prime, requiring a minimum of priming liquid, and all packaged in a single integrated unit having optimum simplicity of use, safety of operation and conservation of blood.

The foregoing detailed description is to be clearly understood as given by way of illustration and example only, the spirit and scope of this invention being limited solely by the appended claims.

I claim:

1. The method of priming and removing air from the blood chamber of a blood oxygenator of the type comprising a spiral tubular membrane of which the interior forms an oxygen flow chamber and including a blood flow chamber wherein blood flows between adjacent windings of the tubular membrane, said method comprising the steps of filling said blood chamber with a priming liquid,
drawing a vacuum within said spiral tubular membrane to at least partly collapse said membrane and enlarge the space between adjacent windings thereof, and
causing said priming liquid to flow into and out of said blood chamber in said blood paths between adjacent windings of said tubular membrane while maintaining a vacuum within said tubular membrane.

2. The method of priming and removing air from the blood chamber of a blood oxygenator of the type comprising a spiral tubular membrane of which the interior forms an oxygen flow chamber and including a blood flow chamber wherein blood flows between adjacent windings of the tubular membrane, said method comprising the steps of filling said blood chamber with a priming liquid,
drawing a vacuum on the interior of said spiral tubular membrane to at least partly collapse said membrane and enlarge the space between adjacent windings thereof, flowing priming liquid into and out of said blood chamber in said blood paths between adjacent windings of said tubular membrane while maintaining decreased pressure within said tubular membrane, and orienting said tubular membrane so that its axis and the length of blood paths between adjacent windings are substantially vertical, said step of flowing priming liquid into and out of said blood chamber comprising flowing priming liquid into an uppermost portion of the chamber and flowing priming liquid out of a lowermost portion of the chamber.

3. A mass transfer system comprising
a closed container,
mass transfer membrane means dividing said container into first and second chamber means,
valve means for passing blood into and out of said first chamber means,
means for passing a fluid into and out of said second chamber means,
a bladder pump having a sealed inflatable and collapsible membrane mounted completely within said first chamber means so as to be completely immersed in the blood therein, and
means for inflating and deflating said pump membrane within said first chamber means to drive blood from said first chamber means and to permit flow of blood into said first chamber means.

4. The system of claim 3 wherein said membrane means comprises a tube wound about a longitudinal axis of said container to provide a plurality of axially directed flow paths between adjacent windings of said tube, said valve means comprising an intake valve at one end of said container and an outlet valve at the other end of said container, said pump membrane being positioned between said intake valve and one end of said mass transfer membrane and very close to at least some of said flow paths, whereby pressure drop between the pump and flow paths is small and secondary higher peak velocity components are imposed upon average blood velocity.

5. The system of claim 4 wherein said axis is oriented in a generally vertical direction, wherein said valves are check valves that are free to open under gravitational force in the absence of differential blood pressure across the valves, wherein inflation of said pump tends to pressurize blood in said first chamber to close said intake valve, open said outlet valve and drive blood through said flow paths to said outlet valve, wherein said intake valve is positioned at the top of said first chamber means and wherein said pump is positioned between said intake valve and said flow paths.

6. The system of claim 5 including means for independently varying volume of blood displaced by said pummp and maximum pressure within said first chamber means.

7. The system of claim 3 wherein said first chamber has input and output portions and includes a plurality of paths for flowing blood from said input to output portions of said chamber, said bladder pump being positioned within said first chamber adjacent upstream ends of said paths to decrease the pressure gradient between said pump and said paths, whereby said pump will produce sharp pressure pulses and a pulsating secondary higher peak velocity component in blood flowing in said paths.

8. A mass transfer system comprising
a closed container,
mass transfer membrane means dividing said container into first and second chamber means,
valve means for passing blood into and out of said first chamber means,
means for passing a fluid into and out of said second chamber means,
a bladder pump having a sealed inflatable and collapsible membrane mounted within said first chamber means, and
means for inflating and deflating said pump membrane within said first chamber means to drive blood from said first chamber means and to permit flow of blood into said first chamber means,
said container being vertically oriented, said mass transfer means providing a plurality of vertical blood passages, said valve means comprising an intake valve at an upper end of said first chamber means and an outlet valve at a lower end of said first chamber means, said bladder pump being located at the upper end of said container.

9. A mass transfer system comprising
a closed container,
mass transfer membrane means dividing said container into first and second chamber means,
valve means for passing blood into and out of said first chamber means,
means for passing a fluid into and out of said second chamber means,
a bladder pump having a sealed inflatable and collapsible membrane mounted within said first chamber means, and
means for inflating and deflating said pump membrane within said first chamber means to drive blood from said first chamber means and to permit flow of blood into said first chamber means,
said membrane means comprising a tube wound about a longitudinal axis of said container to provide a plurality of axially directed flow paths between adjacent windings of said tube, said valve means comprising an intake valve at one end of said container and an outlet valve at the other end of said container, said pump membrane being positioned between said intake valve and one end of said mass transfer membrane and very close to at least some of said flow paths, whereby pressure drop between the pump and flow paths is small and secondary higher peak velocity components are imposed upon average blood velocity,
said container including an axially extending mandrel, said tube being wound about said mandrel, an end collar on an inner end of said tube having a gas fitting projecting from said tube end, a receiver slot in said mandrel receiving said collar, sealing means interposed between said collar and slot, and input gas conduit means in communication with said gas fitting.

10. The system of claim 9 wherein said collar is positioned within said tube and the end of said tube extends over said collar, said tube end being pressed between said collar and said mandrel.

11. The system of claim 9 wherein said gas fitting comprises a tubular connector threaded into said collar and having a head engaging said mandrel, said mandrel including a gas manifold in fluid communication with said tubular connector.

12. In an extracorporeal blood processing system,
a container defining a venous blood reservoir,
a venous blood inlet tube at a lower portion of said container,
a conical baffle extending radially outwardly and slightly downwardly within said container across an upper portion thereof,
said inlet tube including a section extending upwardly within said container through said baffle and having an open upper end positioned adjacent the upper surface of said baffle, whereby blood leaves said inlet tube close to the surface of said baffle and flows downwardly along the surface of the baffle toward the bottom of said reservoir,
means defining a cardiotomy reservoir chamber within said container and positioned above said venous reservoir, means for coupling a vacuum source to said cardiotomy reservoir chamber, a pressurizing valve in said chamber, a float mounted in said chamber to float upon a reservoir of blood within said cardiotomy reservoir chamber, means responsive to said float for operating said pressurizing valve to increase pressure within said cardiotomy reservoir chamber as the level of blood therein rises, and pressure responsive valve means in said cardiotomy reservoir chamber for discharging blood from said cardiotomy reservoir chamber into said venous reservoir upon increase of pressure within said cardiotomy reservoir chamber,
a mass transfer container connected to and below said venous reservoir,
said mass transfer container including a mass transfer membrane dividing the mass transfer container into blood and gas chambers,
a venous reservoir check valve located at the bottom of said venous reservoir for passing venous blood from said venous reservoir into said blood chamber,
a valve for passing blood out of said blood chamber,
means for passing oxygen into and out of said gas chamber,
a bladder pump mounted within said blood chamber adjacent said venous reservoir check valve, and
means for inflating and deflating the bladder pump to increase and decrease the pressure of blood within said blood chamber,
said venous reservoir check valve being normally open in the absence of any differential pressure across the valve, whereby upon expansion of said bladder pump, when said blood chamber and venous reservoir contain blood, said check valve will be driven closed, but whereby said check valve will remain open upon inflation of said bladder pump when said venous reservoir is empty and air is contained within said blood chamber.

13. An extracorporeal blood processing system comprising
a blood gas separator, cardiotomy blood reservoir, and venous blood reservoir, including
a reservoir container,
a partition extending across said reservoir container and dividing it into upper and lower chambers,
a blood gas separator mounted in an upper end of said upper chamber, the lower end of said upper chamber defining said cardiotomy blood reservoir,
means for introducing wound-site blood into said separator,
means for coupling a vacuum source to said upper chamber,
pressure-responsive valve means in said partition for flowing blood from said upper chamber cardiotomy reservoir to said lower chamber,
means for introducing venous blood into said lower chamber for mixing with blood received from said upper chamber, said lower chamber defining said venous reservoir,
a mass transfer system connected to and directly below said venous reservoir,
venous flow check valve means for allowing flow from said venous reservoir to said mass transfer system and for blocking flow from said mass transfer system to said venous reservoir, said mass transfer system comprising
a mass transfer container connected to and below said reservoir container,
a flattened tube wound about a longitudinal axis of said mass transfer container to provide a plurality of axially-directed flow paths between adjacent windings of the tube,
an outlet port in a lower portion of said mass transfer container for flowing arterialized blood from said mass transfer container,
a bladder pump completely located in said mass transfer container between one end of said tube windings and said venous flow valve means so as to be completely immersed in blood contained in said mass transfer container,
means for inflating and deflating said bladder pump, and
means for passing gaseous oxygen through said tube.

14. The system of claim 13 wherein said blood gas separator comprises a large, horizontally disposed substrate and a filter circumscribing said substrate, and further including a generally horizontally disposed conical baffle extending across said upper chamber between said blood gas separator and said partition.

15. The system of claim 13 wherein said venous flow valve means comprises a valve seat formed at a lowermost end of said venous reservoir, a valve stem extending through said valve seat, and a valve closure secured to said stem and adapted to be urged upwardly against said seat, said valve closure being normally open under the force of gravity and in the absence of pressure of inflation of said bladder pump.

16. The system of claim 13 wherein said blood gas separator comprises a horizontally extending distributor tube, a horizontally extending filter circumscribing said distributor tube, and a mesh substrate interposed between the distributor tube and filter.

17. An extracorporeal blood processing system comprising
a blood gas separator, cardiotomy blood reservoir, and venous blood reservoir, including
a reservoir container,
a partition extending across said reservoir container and dividing it into upper and lower chambers,
a blood gas separator mounted in an upper end of said upper chamber, the lower end of said upper chamber defining said cardiotomy blood reservoir, means for introducing wound-site blood into said separator, means for coupling a vacuum source to said upper chamber, pressure-responsive valve means in said partition for flowing blood from said upper chamber cardiotomy reservoir to said lower chamber, means for introducing venous blood into said lower chamber for mixing with blood received from said upper chamber, said lower chamber defining said venous reservoir, a mass transfer system connected to and directly below said venous reservoir, venous flow check valve means for allowing flow from said venous reservoir to said mass transfer system and for blocking flow from said mass transfer system to said venous reservoir, said mass transfer system comprising a mass transfer container connected to and below said reservoir container, a flattened tube wound about a longitudinal axis of said mass transfer container to provide a plurality of axially-directed flow paths between adjacent windings of the tube, an outlet port in a lower portion of said mass transfer container for flowing arterialized blood from said mass transfer container, a bladder pump positioned in said mass transfer container between one end of said tube windings and said venous flow valve means, means for inflating and deflating said bladder pump, means for passing gaseous oxygen through said tube, said blood gas separator comprising a large, horizontally disposed substrate and a filter circumscribing said substrate, and further including a generally horizontally disposed conical baffle extending across said upper chamber between said blood gas separator and said partition, a float in said upper chamber, and a pressurizing valve in said upper chamber for opening the upper chamber to ambient pressure, said pressurizing valve being connected to the float to open when the float rises upon a body of blood contained within said upper chamber.

18. The system of claim 17 including means for indicating the rate of flow of venous blood into said venous reservoir, said last-mentioned means comprising a sharply angulated venous inlet tube having a bend, and a dual leg monometer having first and second legs connected to the inside and outside, respectively, of the bend in said venous inlet tube, said first and second legs extending upwardly from said bend.

* * * * *

UNITED STATES PATENT AND TRADEMARK OFFICE
CERTIFICATE OF CORRECTION

PATENT NO. : 4,490,331

DATED : December 25, 1984

INVENTOR(S) : ROBERT F. STEG, JR.

It is certified that error appears in the above-identified patent and that said Letters Patent is hereby corrected as shown below:

In claim 6 (column 13), line 3, "pummp" should be -- pump --.

Signed and Sealed this

Thirtieth Day of July 1985

[SEAL]

Attest:

DONALD J. QUIGG

Attesting Officer

Acting Commissioner of Patents and Trademarks